United States Patent
Ohno et al.

(10) Patent No.: US 7,517,999 B2
(45) Date of Patent: Apr. 14, 2009

(54) IMIDAZOLIUM COMPOUND

(75) Inventors: Hiroyuki Ohno, Tokyo (JP); Tomonobu Mizumo, Koganei (JP); Masahiro Yoshida, Tokyo (JP); Takayoshi Suga, Tokyo (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 38 days.

(21) Appl. No.: 10/590,549

(22) PCT Filed: Feb. 24, 2005

(86) PCT No.: PCT/JP2005/002988

§ 371 (c)(1), (2), (4) Date: Aug. 23, 2006

(87) PCT Pub. No.: WO2005/080347

PCT Pub. Date: Sep. 1, 2005

(65) Prior Publication Data

US 2007/0191612 A1    Aug. 16, 2007

(30) Foreign Application Priority Data

Feb. 24, 2004  (JP) .......................... 2004-048422

(51) Int. Cl.
C07D 233/58  (2006.01)
H01M 6/16  (2006.01)
(52) U.S. Cl. .................... 548/335.1; 548/341.1; 429/46
(58) Field of Classification Search .............. 548/335.1, 548/341.1
See application file for complete search history.

(56) References Cited

FOREIGN PATENT DOCUMENTS

| CN | 1417407 | | 5/2003 |
|---|---|---|---|
| JP | 03-034270 | * | 2/1991 |
| JP | 2002-145864 | | 5/2002 |
| JP | 2004-047400 | | 2/2004 |
| JP | 2004-035869 | | 2/2005 |
| WO | WO 2004/088671 | | 10/2004 |

OTHER PUBLICATIONS

Qiao, et al, "Acidic ionic modified silica gel as novel solid catalysts for esterification and nitration reactions," Journal of Molecular Catalysis A: Chemical 246 (2006) pp. 65-69.*

Jones et al., "Reactions of Some Allylic and Propargylic Halides with Nucleophiles and Analogous to Those Present in Proteins and Nucleic Acids", Canadian Journal of Chemistry 1971 49:325-332.

* cited by examiner

*Primary Examiner*—Rei-Tsang Shiao
*Assistant Examiner*—Janet L Coppins
(74) *Attorney, Agent, or Firm*—Licata & Tyrrell P.C.

(57) ABSTRACT

A novel imidazolium compound represented by the following general formula (I),

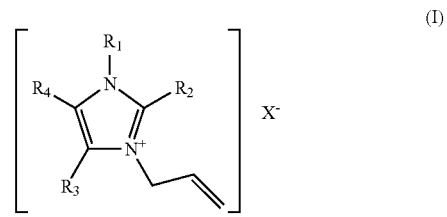

which has an allyl group incorporated in the 3-position of the imidazolium ring. It needs no complicated operations for dissolution and has excellent handleability and a high ionic conductivity.

4 Claims, No Drawings

IMIDAZOLIUM COMPOUND

This patent application is the US National Stage of International Application No. PCT/JP2005/002988, filed Feb. 24, 2005, which claims the benefit of priority from Japanese Application No. 2004-048422, filed Feb. 24, 2004, each of which are herein incorporated by reference in their entirety.

TECHNICAL FIELD

The present invention relates to a novel imidazolium compound that is useful as an electrolyte material for various types of batteries, as a solvent for organic synthesis, as a solvent for separation and extraction, etc.

BACKGROUND ART

In recent years, much attention has been paid to ionic compounds that are liquid at room temperature (ionic liquids), which have high polarity, excellent dissolution performance for various materials, and the properties of being difficult to evaporate, having high ionic conductivity, and being chemically stable, etc. An ionic liquid is formed from a cationic component and an anionic component; in particular, since the cationic component is formed mainly from an organic material, there is the possibility of being able to create a large number of ionic compounds, and the application and development thereof has been anticipated in a wide range of fields such as electrolyte materials for various types of batteries, solvents for organic synthesis in the green chemistry field, solvents for separation and extraction, and organic conductive materials.

As one such ionic compound, an imidazolium compound has been reported. For example, JP, A, 3-34270 describes the use of 1-allyl-3-propylimidazolium chloride as an electrolytic solution of a secondary battery, and JP, A, 2002-145864 describes the use of 1-allyl-3-propylimidazolium iodide as an electrolyte of a wet solar battery. Furthermore, 'Canadian Journal of Chemistry', 1971, Vol. 49, pp. 325-332 describes 1-methyl-3-allylimidazolium bromide, 1,3-diallylimidazolium bromide, etc. However, with regard to a compound having an allyl group at the 1-position or 3-position of the imidazolium ring, no compounds other than those described in the above publications are known.

Among the ionic imidazolium compounds, there are those that are solid at room temperature, those that have high viscosity, those that have low ionic conductivity, etc., depending on the type of anionic group. These properties become a problem when the imidazolium compound is used as an electrolyte material for various types of batteries, a solvent for organic synthesis, a solvent for separation and extraction, etc. For example, there are the problems that it is necessary to dissolve those that are solid at room temperature in another organic solvent each time when they are used as a reaction solvent or an extraction solvent, it might be difficult to handle those that have high viscosity, particularly in the field of electrolytes, reaction solvents, etc., and those having low ionic conductivity cannot give satisfactory effects when they are used as a reaction solvent, an electrolyte, etc.

Because of this, for example, as an electrolyte or electrolytic solution for a lithium secondary battery, in order to enable its use under severe environments, there is a strong desire for it to be a liquid that has as low viscosity as an organic solvent at very low temperature (e.g. $-40°$ C.), and as a solvent for an organic synthesis reaction there is a strong desire for it to be able to be used at very low temperature to high temperature (e.g. $250°$ C.) from the viewpoint of ease of handling and freedom in setting a reaction temperature.

Furthermore, compounds that are currently used as organic solvents have the serious problem that they badly affect the environment and animals and plants in terms of air pollution, water pollution, destruction of the ozone layer, etc. In particular, since the effect due to halogen-containing organic solvents is serious, regulations on their use, production, etc. have been tightened. There is therefore a desire for an organic solvent that has a performance that is the same as or higher than the above organic solvents but that does not affect the environment.

DISCLOSURE OF INVENTION

Problems to be Solved by the Invention

It is therefore an object of the present invention to provide a novel imidazolium compound that is a liquid at room temperature and has low viscosity and high ionic conductivity, a solvent that does not require a complicated dissolution operation and has excellent dissolution performance for various types of materials, and an electrolyte material that is easy to handle and has high ionic conductivity.

Means of Solving the Problems

As a result of an intensive investigation by the present inventors in order to solve the above-mentioned problems, it has been found that by introducing an allyl group at the 1-position and/or 3-position of an imidazole ring an imidazolium compound that is solid at room temperature liquefies, and not only does the viscosity decrease, but the ionic conductivity also improves; it has also been found that an ionic liquid that is suitable as a solvent for organic synthesis, a solvent for an extraction solvent, or an electrolyte material can be obtained, and the present invention has thus been accomplished.

That is, the imidazolium compound of the present invention is represented by Formula (I) below:

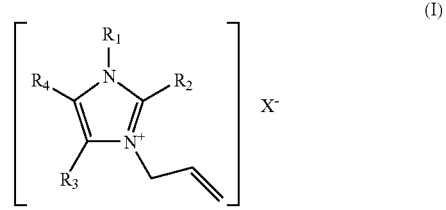

(I)

In which, $R_1$, $R_2$, $R_3$, and $R_4$ independently denote a hydrogen atom, an optionally substituted alkyl group having 1 to 10 carbon atoms, an optionally substituted cycloalkyl group having 3 to 10 carbon atoms, an optionally substituted alkenyl group having 2 to 10 carbon atoms, or an optionally substituted aryl group having 6 to 10 carbon atoms, and $X^-$ is $Cl^-$, $Br^-$, $I^-$, $BF_4^-$, $PF_6^-$, $CF_3SO_3^-$, or $(CF_3SO_2)_2N^-$, with the proviso that when $R_1$ is an alkyl group having 1 to 3 carbon atoms, $X^-$ is $BF_4^-$, $PF_6^-$, $CF_3SO_3^-$, or $(CF_3SO_2)_2N^-$, and a case in which $R_2$ to $R_4$ are hydrogen atoms, $R_1$ is an allyl group, and $X^-$ is $Br^-$ is excluded.

$R_1$ is preferably an alkyl group having 4 to 8 carbon atoms or an alkenyl group having 2 to 4 carbon atoms, and particularly preferably an allyl group.

The solvent of the present invention contains an imidazolium compound represented by Formula (I) below:

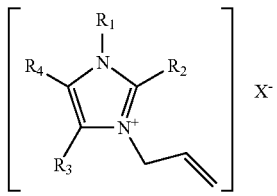

In which, $R_1$, $R_2$, $R_3$, and $R_4$ independently denote a hydrogen atom, an optionally substituted alkyl group having 1 to 10 carbon atoms, an optionally substituted cycloalkyl group having 3 to 10 carbon atoms, an optionally substituted alkenyl group having 2 to 10 carbon atoms, or an optionally substituted aryl group having 6 to 10 carbon atoms, and $X^-$ is $Cl^-$, $Br^-$, $I^-$, $BF_4^-$, $PF_6^-$, $CF_3SO_3^-$, or $(CF_3SO_2)_2N^-$.

The electrolyte material of the present invention is an electrolyte material containing an imidazolium compound represented by Formula (I) above, wherein $X^-$ is $BF_4^-$, $PF_6^-$, $CF_3SO_3^-$, or $(CF_3SO_2)_2N^-$.

EFFECTS OF INVENTION

With regard to the imidazolium compound of the present invention, by introducing an allyl group at the 1-position and/or the 3-position of the imidazolium ring a compound that is solid at room temperature can be made into a liquid. Because of this, when it is used as a solvent of an organic synthesis reaction, etc., a step of dissolving the imidazolium compound can be omitted, and the operability improves due to a decrease in viscosity. Furthermore, since the ionic conductivity improves as a result of introducing an allyl group, it has excellent properties as an ionic liquid and an electrolyte material for various types of batteries, etc. Moreover, the imidazolium compound of the present invention is suitable as an organic conductive material due to the effect of the allyl group.

The imidazolium compound of the present invention is represented by Formula (I) below.

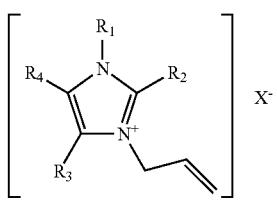

In Formula (I), the optionally substituted alkyl group having 1 to 10 carbon atoms denoted by $R_1$, $R_2$, $R_3$, and $R_4$ may be straight chain or branched chain, and specific examples thereof include a methyl group, an ethyl group, a n-propyl group, an isopropyl group, a n-butyl group, an isobutyl group, a sec-butyl group, a tert-butyl group, a n-pentyl group, an isopentyl group, a n-hexyl group, a n-heptyl group, and a n-octyl group. From the viewpoint of ease of handling of the imidazolium compound, $R_1$ is preferably an alkyl group having 1 to 8 carbon atoms, and particularly preferably a pentyl group, an octyl group, etc. $R_2$ to $R_4$ are preferably lower alkyl groups such as a methyl group, an ethyl group, or a propyl group.

Examples of the optionally substituted cycloalkyl group having 3 to 10 carbon atoms denoted by $R_1$ to $R_4$ include a cyclopentyl group, a methylcyclopentyl group, a dimethylcyclopentyl group, a cyclohexyl group, and a methylcyclohexyl group. Among them, from the viewpoint of ease of handling of the imidazolium compound, a cyclopentyl group, a cyclohexyl group, etc. are preferable.

The optionally substituted alkenyl group having 2 to 10 carbon atoms denoted by $R_1$ to $R_4$ may be straight chain or branched chain, and examples thereof include a vinyl group, a 1-propenyl group, a 2-propenyl(allyl) group, a 2-butenyl (crotyl) group, and a 3-butenyl group. From the viewpoint of ease of handling of the imidazolium compound and the ionic conductivity, an alkenyl group having 2 to 4 carbon atoms is preferable, and an allyl group is particularly preferable.

Examples of the optionally substituted aryl group having 6 to 10 carbon atoms denoted by $R_1$ to $R_4$ include a phenyl group, a tolyl group, a xylyl group, and a naphthyl group. Among them, from the viewpoint of ease of handling of the imidazolium compound a phenyl group, etc. is preferable.

Examples of groups with which the above-mentioned alkyl group, cycloalkyl group, alkenyl group, and aryl group can be substituted include halogens (Cl, Br, I, etc.), a hydroxyl group, a cyano group, a carbonyl group, an ester group, an ether group, and a nitro group. The number of these substitutents is not particularly limited, but it is normally 1 to 2.

Preferred examples of the cationic component in which $R_1$, $R_2$, $R_3$, and $R_4$ are combined include 1-methyl-3-allylimidazolium, 1-ethyl-3-allylimidazolium, 1-n-propyl-3-allylimidazolium, 1-isopropyl-3-allylimidazolium, 1-n-butyl-3-allylimidazolium, 1-isobutyl-3-allylimidazolium, 1-sec-butyl-3-allylimidazolium, 1-tert-butyl-3-allylimidazolium, 1-n-pentyl-3-allylimidazolium, 1-isopentyl-3-allylimidazolium, 1-n-hexyl-3-allylimidazolium, 1-n-heptyl-3-allylimidazolium, 1-n-octyl-3-allylimidazolium, 1,3-diallylimidazolium, 1-cyclopentyl-3-allylimidazolium, 1-methylcyclopentyl-3-allylimidazolium, 1-cyclohexyl-3-allylimidazolium, 1-vinyl-3-allylimidazolium, 1-(1-propenyl)-3-allylimidazolium, 1-(2-butenyl)-3-allylimidazolium, and 1-(3-butenyl)-3-allylimidazolium. Among them, as a solvent such as a reaction solvent or as an electrolyte material, 1-methyl-3-allylimidazolium, 1-ethyl-3-allylimidazolium, 1-n-propyl-3-allylimidazolium, 1-butyl-3-allylimidazolium, 1,3-diallylimidazolium, etc. are preferable.

In Formula (I), $X^-$ is $Cl^-$, $Br^-$, $I^-$, $BF_4^-$, $PF_6^-$, $CF_3SO_3^-$ or $(CF_3SO_2)_2N^-$. In the imidazolium compound of the present invention, when $R_1$ is an alkyl group having 1 to 3 carbon atoms, $X^-$ is $BF_4^-$, $PF_6^-$, $CF_3SO_3^-$, or $(CF_3SO_2)_2N^-$. When the imidazolium compound represented by Formula (I) is used as a solvent, $X^-$ is not particularly limited as long as it is the above-mentioned anion. When the imidazolium compound represented by Formula (I) is used as an electrolyte material, $X^-$ is preferably $BF_4^-$, $PF_6^-$, $CF_3SO_3^-$, or $(CF_3SO_2)_2N^-$ from the viewpoint of ionic conductivity.

Since the imidazolium compound represented by Formula (I) has good ionic conductivity, it can be used preferably as an electrolyte material for various types of batteries (lithium secondary battery, solar battery, fuel battery, etc.), etc. For example, when it is used as an electrolyte for a lithium secondary battery, the above-mentioned imidazolium compound may be used, together with a lithium salt, as main components of the electrolyte. The lithium salt is not particularly limited, and $LiBF_4$, $LiPF_6$, $LiClO_4$, $LiCF_3SO_3$, $LiN(CF_3SO_2)_2$, $LiN(C_2F_5SO_2)_2$, $LiN(CF_3SO_2)(C_4F_9SO_2)$, $LiC(CF_3SO_2)_3$, $LiC$ ($C_2F_5SO_2)_3$, etc. may be used, and they may be used singly or in a combination of two or more types.

Furthermore, the electrolyte for the lithium secondary battery may contain a macromolecular compound in combination with the lithium salt and the imidazolium compound. Examples of the macromolecular compound include polyethylene oxide, polypropylene oxide, polyacrylonitrile, polymethyl methacrylate, polyvinylidene fluoride, and polymers of monomers such as an acrylic monomer, a methacrylic monomer, an acrylamide type monomer, an allyl type monomer, and a styrene type monomer. They may be used singly or in a combination of two or more types.

The imidazolium compound represented by Formula (I) is also suitable as an electrolyte material of an electrolytic solution for an electrolytic capacitor, an electric double layer capacitor, a proton conducting secondary battery, an electrochromic display device, etc. The electrolytic solution may employ one or more types of imidazolium compounds, or may be used as a mixture with a predetermined organic solvent. Examples of the organic solvent include butyl alcohol, diacetone alcohol, benzyl alcohol, an amino alcohol, ethylene glycol, propylene glycol, diethylene glycol, hexylene glycol, phenyl glycol, ethylene glycol monomethyl ether, diethylene glycol monomethyl ether, diethylene glycol monoethyl ether, ethylene glycol monophenyl ether, ethylene glycol dimethyl ether, ethylene glycol diethyl ether, diethylene glycol dimethyl ether, diethylene glycol diethyl ether, N-methylformamide, N,N-dimethylformamide, N,N-diethylformamide, N,N-dimethylacetamide, N,N-dimethylpropionamide, acetonitrile, methoxyacetonitrile, butyronitrile, propionitrile, 3-methoxypropionitrile, nitromethane, nitroethane, dimethylsulfoxide, γ-butyrolactone, β-butyrolactone, γ-valerolactone, δ-valerolactone, sulfolane, 3-methylsulfolane, 1,3-dimethyl-2-imidazolidinone, 3-methyl-2-oxazolidone, ethyl carbonate, ethylene carbonate, and propylene carbonate. These organic solvents may be used singly or in a combination of two or more types.

The imidazolium compound represented by Formula (I) in which an allyl group has been introduced at the 3-position of the imidazole ring may be used preferably as an organic solvent since it liquefies at room temperature. In accordance with the introduction of an allyl group into the imidazole ring, the viscosity is reduced thus improving the ease of handling as an organic solvent, the ionic conductivity is increased thus improving the polarity of the compound itself, and it has high performance as an organic solvent. Furthermore, since the imidazolium compound is nonvolatile and has high thermal stability, an organic solvent containing said compound has little effect on the environment and can be reused by recovering it. In this way, the solvent of the present invention exhibits excellent effects that cannot be achieved by conventional organic solvents.

When the imidazolium compound represented by Formula (I) is used as a solvent for organic synthesis, a solvent for separation and extraction, etc., the imidazolium compound is a salt that is present as a liquid preferably at 25° C. or greater, more preferably at 0° C. or greater, and yet more preferably −10° C. or greater.

As a solvent, one or more types of imidazolium compound represented by Formula (I) may be used singly or as a mixture with another solvent. Said other solvent is not particularly limited, and examples thereof include alcohols (methyl alcohol, ethyl alcohol, propyl alcohol, butyl alcohol, benzyl alcohol, ethylene glycol, propylene glycol, diethylene glycol, glycerol, etc.), ethers (diethyl ether, tetrahydrofuran, dioxane, diglyme, ethylene glycol monomethyl ether, ethylene glycol monophenyl ether, ethylene glycol dimethyl ether, etc.), amides (N-methylformamide, N,N-dimethylformamide, N-ethylacetamide, N,N-diethylacetamide, N,N-dimethylpropionamide, etc.), oxazolidinones (1,3-dimethyl-2-imidazolidinone, 3-methyl-2-oxazolidone, etc.), ketones (acetone, methyl ethyl ketone, methyl isobutyl ketone, cyclohexanone, etc.), nitriles (acetonitrile, propionitrile, acrylonitrile, etc.), esters (ethyl acetate, trimethyl phosphate, etc.), sulfoxides (dimethylsulfoxide, etc.), halohydrocarbons (methylene chloride, etc.), aromatic compounds (benzene, toluene, xylene, etc.), paraffins (hexane, cyclohexane, octane, isooctane, etc.), lactones (γ-butyrolactone, α-acetyl-γ-butyrolactone, β-butyrolactone, etc.), and aqueous solvents. They may be used as a mixture of two or more types.

A process for producing the imidazolium compound represented by Formula (I) is not particularly limited, and may employ a known method as appropriate. For example, it may be obtained by reacting a 1- or 3-substituted imidazole with a compound RY having a predetermined substituent (R has the same meaning as $R_1$ in Formula (I), and Y is a leaving group such as a halogen) and by the further action of $APF_6$, A(TFSI) (A denotes a cation such as $NH_4^+$ or $Li^+$, and (TFSI) denotes $(CF_3SO_2)_2N^-$), etc.

EXAMPLES

The present invention is explained in further detail below by way of Examples, but the present invention is not limited to the Examples below.

Example 1

Synthesis of 1-butyl-3-allylimidazolium bromide

1-Allylimidazole (1.0 mL: 0.009 mol) was ice-cooled, and n-butyl bromide (2.97 mL: 0.28 mol) was added thereto dropwise. After the dropwise addition, the temperature was gradually increased to 25° C., and subsequently stirring was carried out continuously for 24 hours. The product was a pale brown viscous liquid. This was added dropwise to 100 mL of toluene, and a viscous liquid that separated out was recovered and dried. The same procedure was repeated once more. The viscous liquid thus obtained was made into an acetonitrile solution, active carbon that had been heated and vacuum-dried was added thereto, and stirring was carried out for about 24 hours. After the acetonitrile was distilled off, the viscous liquid was recovered with dichloromethane, and the solvent was distilled off. The 1-butyl-3-allylimidazolium bromide thus obtained was a liquid at room temperature, the amount collected was 1.93 g (yield; 85%), the glass transition temperature (T.g) was −62.5° C., and the ionic conductivity at 30° C. was 0.533 (mS/cm). The results are given in Table 1. The structure was confirmed by $^1$H-NMR measurement. The results are shown below.

$^1$H-NMR (CDCl$_3$, Me$_4$Si) δ 0.88-0.95 (3H, t, —CH$_2$—CH$_3$), 1.21-1.43 (2H, m, N—CH$_2$—CH$_2$—CH$_2$—CH$_3$), 1.80-2.00 (2H, m, N—CH$_2$—CH$_2$—CH$_2$—CH$_3$), 4.34-4.37 (2H, t, N—CH$_2$—CH$_2$—), 5.06-5.09 (2H, d, N—CH$_2$—CH=), 5.46-5.51 (2H, m, —CH=CH$_2$), 6.03-6.08 (1H, m, N—CH$_2$—CH=CH$_2$), 7.43 (1H, s, =CH—N—), 7.46 (1H, s, =CH—N—), 10.5 (1H, s, —N=CH—N—)

Example 2

Synthesis of 1-pentyl-3-allylimidazolium bromide

1-Allylimidazole (1.0 mL: 0.009 mol) was ice-cooled, and pentyl bromide (3.43 mL: 0.28 mol) was added thereto dropwise. After the dropwise addition, the temperature was gradually increased to 25° C., and subsequently stirring was carried out continuously for 24 hours. The product was a pale brown viscous liquid. This was added dropwise to 100 mL of toluene, and a viscous liquid that separated out was recovered and dried. The same procedure was repeated once more. The viscous liquid thus obtained was made into an acetonitrile solution, active carbon that had been heated and vacuum-dried was added thereto, and stirring was carried out for about 24 hours. After the acetonitrile was distilled off, the viscous liquid was recovered with dichloromethane, and the solvent was distilled off. The 1-pentyl-3-allylimidazolium bromide thus obtained was a liquid at room temperature, the amount collected was 2.16 g (yield; 90%), the glass transition temperature (Tg) was −61.3° C., and the ionic conductivity at 30° C. was 0.244 (mS/cm). The results are given in Table 1. The structure was confirmed by $^1$H-NMR measurement. The results are shown below.

$^1$H-NMR (CDCl$_3$, Me$_4$Si) δ 0.89-0.92 (3H, t, —CH$_2$—CH$_3$), 1.28-1.42 (4H, m, N—CH$_2$—CH$_2$—CH$_2$—CH$_2$—CH$_3$), 1.87-2.02 (2H, m, N—CH$_2$—CH$_2$—CH$_2$—CH$_2$—CH$_3$), 4.34-4.37 (2H, t, N—CH$_2$—CH$_2$—), 5.06-5.08 (2H, d, N—CH$_2$—CH=), 5.46-5.52 (2H, m, —CH=CH$_2$), 6.02-6.07 (1H, m, N—CH$_2$—CH=CH$_2$), 7.44 (1H, s, =CH—N—), 7.47 (1H, s, =CH—N—), 10.6 (1H, s, —N=CH—N—)

Example 3

Synthesis of 1-octyl-3-allylimidazolium bromide

1-Allylimidazole (1.0 mL: 0.009 mol) was ice-cooled, and octyl bromide (4.8 mL: 0.028 mol) was added thereto dropwise. After the dropwise addition, the temperature was gradually increased to 25° C., and subsequently stirring was carried out continuously for 24 hours. The product was a pale brown viscous liquid. This was added dropwise to 100 mL of toluene, and a viscous liquid that separated out was recovered and dried. The same procedure was repeated once more. The viscous liquid thus obtained was made into an acetonitrile solution, active carbon that had been heated and vacuum-dried was added thereto, and stirring was carried out for about 24 hours. After the acetonitrile was distilled off, the viscous liquid was recovered with dichloromethane, and the solvent was distilled off. The 1-octyl-3-allylimidazolium bromide thus obtained was a liquid at room temperature, the amount collected was 2.47 g (yield; 89%), the glass transition temperature (Tg) was −64.5° C., and the ionic conductivity at 30° C. was 0.0926 (mS/cm). The results are given in Table 1. The structure was confirmed by $^1$H-NMR measurement. The results are shown below.

$^1$H-NMR (CDCl$_3$, Me$_4$Si) δ 0.86-0.88 (3H, t, —CH$_2$—CH$_3$), 1.95-1.43 (10H, m, N—CH$_2$—CH$_2$—CH$_2$—CH$_2$—CH$_2$—CH$_2$—CH$_2$—CH$_3$), 1.85-2.01 (2H, m, N—CH$_2$—CH$_2$—CH$_2$), 4.33-4.36 (2H, t, N—CH$_2$—CH$_2$—), 5.07-5.08 (2H, d, N—CH$_2$—CH=), 5.47-5.52 (2H, m, —CH=CH$_2$), 6.02-6.07 (1H, m, N—CH$_2$—CH=CH$_2$), 7.42 (1H, s, =CH—N—), 7.43 (1H, s, =CH—N—), 10.6 (1H, s, —N=CH—N—)

Example 4

Synthesis of 1,3-diallylimidazolium chloride

An acetonitrile 2.0 mL solution of 1-allylimidazole (1.0 mL: 0.009 mol) was made, and allyl chloride (2.25 mL: 0.028 mol) was added dropwise thereto. Subsequently, this solution was heated at 70° C. and stirred for 24 hours. The acetonitrile was distilled off to give a pale brown viscous liquid. This was added dropwise to 150 mL of toluene, and a viscous liquid that separated out was recovered and dried. The same procedure was repeated once more. The viscous liquid thus obtained was made into an acetonitrile solution, active carbon that had been heated and vacuum-dried was added thereto, and stirring was carried out for about 48 hours. After the acetonitrile was distilled off, the viscous liquid was recovered with dichloromethane, and the solvent was distilled off. The 1,3-diallylimidazolium chloride thus obtained was a liquid at room temperature, the amount collected was 1.33 g (yield; 78.3%), the glass transition temperature (Tg) was −59.9° C., and the ionic conductivity at 30° C. was 0.0773 mS/cm. The results are given in Table 1. The structure was confirmed by $^1$H-NMR measurement. The results are shown below.

$^1$H-NMR (CDCl$_3$, Me$_4$Si) δ 5.05-5.06 (4H, d, N—CH$_2$—CH=), 5.45-5.50 (4H, m, —CH=CH$_2$), 6.00-6.08 (2H, m, N—CH$_2$—CH=CH$_2$), 7.56 (2H, s, =CH—N—), 10.7 (1H, s, —N=CH—N—)

Example 5

Synthesis of 1,3-diallylimidazolium iodide

1-Allylimidazole (1.0 mL: 0.009 mol) was ice-cooled, and allyl iodide (2.51 mL: 0.028 mol) was added thereto dropwise. Subsequently, the temperature was gradually increased to 25° C., and subsequently stirring was carried out continuously for 24 hours. The product was a pale brown viscous liquid. This was added dropwise to 200 mL of toluene, and a viscous liquid that separated out was recovered and dried. The same procedure was repeated once more. The viscous liquid thus obtained was made into an acetonitrile solution, active carbon that had been heated and vacuum-dried was added thereto, and stirring was carried out for about 48 hours. After the acetonitrile was distilled off, the viscous liquid was recovered with dichloromethane, and the solvent was distilled off. The 1,3-diallylimidazolium iodide thus obtained was a liquid at room temperature, the amount collected was 1.81 g (yield; 71.3%), the glass transition temperature (Tg) was −68.1° C., and the ionic conductivity at 30° C. was 1.32 mS/cm. The results are given in Table 1. The structure was confirmed by $^1$H-NMR measurement. The results are shown below.

$^1$H-NMR (CDCl$_3$, Me$_4$Si) δ 5.03-5.04 (4H, d, N—CH$_2$—CH=), 5.50-5.57 (4H, m, —CH=CH$_2$), 6.04-6.12 (2H, m, N—CH$_2$—CH=CH$_2$), 7.47 (2H, s, =CH—N—), 10.0 (1H, s, —N=CH—N—)

Example 6

Synthesis of 1-butyl-3-allylimidazolium tetrafluoroborate

After making 1-butyl-3-allylimidazolium bromide (1.00 g; 0.0041 mol) obtained in Example 1 into a 40 mL aqueous solution, NH$_4$BF$_4$ (0.47 g: 0.0045 mol) was added thereto, and stirring was carried out at room temperature for a few hours. By carrying out an anion exchange reaction in this aqueous solution 1-butyl-3-allylimidazolium tetrafluoroborate was produced. After the water was distilled off from the reaction solution, 200 mL of methylene chloride was added thereto, and the insoluble content was filtered off. After the methylene chloride was distilled off from the filtrate, a 0.1 M aqueous solution of silver nitrate was added to the viscous liquid thus obtained, and the insoluble content was filtered off. The same procedure was repeated two more times, and it was confirmed that no insoluble content was formed in the aqueous solution of silver nitrate. After the water was distilled off from the filtrate, the viscous liquid thus obtained was dissolved in 100 mL of methylene chloride, magnesium sulfate was added thereto, and the mixture was left to stand for a few hours. After filtering off the magnesium sulfate and silver nitrate, the filtrate was dried. The methylene chloride was distilled off to give a viscous liquid. The 1-butyl-3-allylimidazolium tetrafluoroborate thus obtained was a liquid at room temperature, the amount collected was 0.73 g (yield; 71%), the glass transition temperature (Tg) was −89.0° C., and the ionic conductivity at 30° C. was 1.22 mS/cm. The results are given in Table 1. The structure was confirmed by $^1$H-NMR measurement. The results are shown below.

$^1$H-NMR (CDCl$_3$, Me$_4$Si) δ 0.88-0.95 (3H, t, —CH$_2$—CH$_3$), 1.21-1.43 (2H, m, N—CH$_2$—CH$_2$—CH$_2$—CH$_3$), 1.85-2.06 (2H, m, N—CH$_2$—CH$_2$—CH$_2$—CH$_3$), 3.99-4.05 (2H, t, N—CH$_2$—CH$_2$—), 4.78-4.79 (2H, d, N—CH$_2$—CH=), 5.45-5.52 (2H, m, —CH=CH$_2$), 5.93-6.02 (1H, m, N—CH$_2$—CH=CH$_2$), 7.32 (1H, s, =CH—N—), 7.38 (1H, s, =CH—N—), 8.80 (1H, s, —N=CH—N—)

Example 7

Synthesis of 1-butyl-3-allylimidazolium hexafluorophosphate

After making 1-butyl-3-allylimidazolium bromide (1.00 g; 0.0041 mol) obtained in Example 1 into a 40 mL aqueous solution, NH$_4$PF$_6$ (0.73 g: 0.0045 mol) was added thereto, and stirring was carried out at room temperature for a few hours. By carrying out an anion exchange reaction in this aqueous solution 1-butyl-3-allylimidazolium hexafluorophosphate was produced. Since the product was hydrophobic, it separated as a phase from the aqueous phase. 100 mL of methylene chloride was added to the reaction solution, and separation into two phases occurred. The methylene chloride phase was collected, magnesium sulfate was added thereto, and the mixture was left to stand for a few hours. After filtering off the magnesium sulfate, the filtrate was dried. The methylene chloride was distilled off to give a viscous liquid. The 1-butyl-3-allylimidazolium hexafluorophosphate thus obtained was a liquid at room temperature, the amount collected was 1.0 g (yield; 77.3%), the glass transition temperature (Tg) was −85.2° C., and the ionic conductivity at 30° C. was 1.01 mS/cm. The results are given in Table 1. The structure was confirmed by $^1$H-NMR measurement. The results are shown below.

$^1$H-NMR (CDCl$_3$, Me$_4$Si) δ 0.88-0.95 (3H, t, —CH$_2$—CH$_3$), 1.21-1.43 (2H, m, N—CH$_2$—CH$_2$—CH$_2$—CH$_3$), 1.80-2.00 (2H, m, N—CH$_2$—CH$_2$—CH$_2$—CH$_3$), 4.01-4.06 (2H, t, N—CH$_2$—CH$_2$—), 4.78-4.79 (2H, d, N—CH$_2$—CH=), 5.45-5.52 (2H, m, —CH=CH$_2$), 5.93-6.02 (1H, m, N—CH$_2$—CH=CH$_2$), 7.32 (1H, s, =CH—N—), 7.38 (1H, s, =CH—N—), 8.60 (1H, s, —N=CH—N—)

Example 8

Synthesis of 1-butyl-3-allylimidazolium bis(trifluoromethylsulfonyl)imide

After making 1-butyl-3-allylimidazolium bromide (1.00 g; 0.0041 mol) obtained in Example 1 into a 40 mL aqueous solution, lithium bis(trifluoromethylsulfonyl)imide salt (1.23 g: 0.0045 mol) was added thereto, and stirring was carried out at room temperature for a few hours. By carrying out an anion exchange reaction in this aqueous solution 1-butyl-3-al-lylimidazolium bis(trifluoromethylsulfonyl)imide was produced. Since the product was hydrophobic, it separated as a phase from the aqueous phase. 80 mL of chloroform was added to the reaction solution, and separation into two phases occurred. The chloroform phase was collected, magnesium sulfate was added thereto, and the mixture was left to stand for a few hours. After filtering off the magnesium sulfate, the filtrate was dried. The chloroform was distilled off to give a liquid product. The 1-butyl-3-allylimidazolium bis(trifluoromethylsulfonyl)imide thus obtained was a liquid at room temperature, the amount collected was 1.67 g (yield; 92%), the glass transition temperature (Tg) was −90.0° C., and the ionic conductivity at 30° C. was 1.53 mS/cm. The results are given in Table 1. The structure was confirmed by $^1$H-NMR measurement. The results are shown below.

$^1$H-NMR (CDCl$_3$, Me$_4$Si) δ 0.88-0.95 (3H, t, —CH$_2$—CH$_3$), 1.20-1.43 (2H, m, N—CH$_2$—CH$_2$—CH$_2$—CH$_3$), 1.81-2.02 (2H, m, N—CH$_2$—CH$_2$—CH$_2$—CH$_3$), 4.00-4.06 (2H, t, N—CH$_2$—CH$_2$—), 4.80-4.81 (2H, d, N—CH$_2$—CH=), 5.46-5.51 (2H, m, —CH=CH$_2$), 5.93-6.01 (1H, m, N—CH$_2$—CH=CH$_2$), 7.31 (1H, s, =CH—N—), 7.37 (1H, s, =CH—N—), 8.70 (1H, s, —N=CH—N—)

Example 9

Synthesis of 1,3-diallylimidazolium tetrafluoroborate

After making diallylimidazolium bromide (1.00 g; 0.0044 mol) obtained by the same method as in Example 5 into a 40 mL aqueous solution, NH$_4$BF$_4$ (0.50 g: 0.0048 mol) was added thereto, and stirring was carried out at room temperature for a few hours. By carrying out an anion exchange reaction in this aqueous solution 1,3-diallylimidazolium tetrafluoroborate was produced. After water was distilled off from the reaction solution, 200 mL of methylene chloride was added thereto, and the insoluble content was filtered off. After the methylene chloride was distilled off from the filtrate, a 0.1 M aqueous solution of silver nitrate was added to the viscous liquid thus obtained, and the insoluble content was filtered off. The same procedure was repeated two more times, and it was confirmed that no insoluble content was formed in the aqueous solution of silver nitrate. After the water was distilled off from the reaction solution, the viscous liquid thus obtained was dissolved in 100 mL of methylene chloride, magnesium sulfate was added thereto, and the mixture was left to stand for a few hours. After filtering off the magnesium sulfate and silver nitrate, the filtrate was dried. The methylene chloride was distilled off to give a liquid product. The 1,3-diallylimidazolium tetrafluoroborate thus obtained was a liquid at room temperature, the amount collected was 0.75 g (yield; 73%), the glass transition temperature (Tg) was −90.4° C., and the ionic conductivity at 30° C. was 2.44 mS/cm. The results are given in Table 1. The structure was confirmed by $^1$H-NMR measurement. The results are shown below.

$^1$H-NMR (CDCl$_3$, Me$_4$Si) δ 4.77-4.78 (4H, d, N—CH$_2$—CH=), 5.44-5.51 (4H, m, —CH=CH$_2$), 5.98-6.04 (2H, m, N—CH$_2$—CH=CH$_2$), 7.34 (2H, s, =CH—N—), 8.58 (1H, s, —N=CH—N—)

Example 10

Synthesis of 1,3-diallylimidazolium hexafluorophosphate

After making diallylimidazolium bromide (1.00 g; 0.0044 mol) obtained by the same method as in Example 5 into a 40 mL aqueous solution, $NH_4PF_6$ (0.78 g: 0.0048 mol) was added thereto, and stirring was carried out at room temperature for a few hours. By carrying out an anion exchange reaction in this aqueous solution 1,3-diallylimidazolium hexafluorophosphate was produced. Since the product was hydrophobic, it separated as a phase from the aqueous phase. 100 mL of methylene chloride was added to the reaction solution, and separation into two phases occurred. The methylene chloride phase was collected, magnesium sulfate was added thereto, and the mixture was left to stand for a few hours. After filtering off the magnesium sulfate, the filtrate was dried. The methylene chloride was distilled off to give a viscous liquid. This crystallized upon cooling. The 1,3-diallylimidazolium hexafluorophosphate thus obtained was a liquid at room temperature, the amount collected was 1.0 g (yield; 77.3%), the melting point was 16.7° C., and the ionic conductivity at 30° C. was 1.99 mS/cm. The results are given in Table 1. The structure was confirmed by $^1$H-NMR measurement. The results are shown below.

$^1$H-NMR (CDCl$_3$, Me$_4$Si) δ 4.78-4.79 (4H, d, N—CH$_2$—CH=), 5.44-5.51 (4H, m, —CH=CH$_2$), 5.98-6.03 (2H, m, N—CH$_2$—CH=CH$_2$), 7.34 (2H, s, =CH—N—), 8.62 (1H, s, —N=CH—N—)

Example 11

Synthesis of 1,3-diallylimidazolium bis(trifluoromethylsulfonyl)imide

After making diallylimidazolium bromide (1.00 g; 0.0044 mol) obtained by the same method as in Example 5 into a 20 mL aqueous solution, lithium bis(trifluoromethylsulfonyl)imide salt (1.38 g: 0.0048 mol) was added thereto, and stirring was carried out at room temperature for a few hours. By carrying out an anion exchange reaction in this aqueous solution 1,3-diallylimidazolium bis(trifluoromethylsulfonyl)imide was produced. Since the product was hydrophobic, it separated as a phase from the aqueous phase. 80 mL of chloroform was added to the reaction solution, and separation into two phases occurred. The chloroform phase was collected, magnesium sulfate was added thereto, and the mixture was left to stand for a few hours. After filtering off the magnesium sulfate, the filtrate was dried. The chloroform was distilled off to give a liquid product. The 1,3-diallylimidazolium bis(trifluoromethylsulfonyl)imide thus obtained was a liquid at room temperature, the amount collected was 1.79 g (yield; 95%), the glass transition temperature (Tg) was −91.6° C., and the ionic conductivity at 30° C. was 2.63 mS/cm. The results are given in Table 1. The structure was confirmed by $^1$H-NMR measurement. The results are shown below.

$^1$H-NMR (CDCl$_3$, Me$_4$Si) δ 4.80-4.81 (4H, d, N—CH$_2$—CH=), 5.46-5.51 (4H, m, —CH=CH$_2$), 5.95-6.03 (2H, m, N—CH$_2$—CH=CH$_2$), 7.32 (2H, s, =CH—N—), 8.76 (1H, s, —N=CH—N—)

TABLE 1

| Example No. | R$_1$ | R$_3$ | X$^-$ | Tg | Ionic conductivity |
|---|---|---|---|---|---|
| Example 1 | Butyl | Allyl | Br$^-$ | −62.5° C. | 0.533 mS/cm |
| Example 2 | Pentyl | Allyl | Br$^-$ | −61.3° C. | 0.244 mS/cm |
| Example 3 | Octyl | Allyl | Br$^-$ | −64.5° C. | 0.0926 mS/cm |
| Example 4 | Allyl | Allyl | Cl$^-$ | −59.9° C. | 0.0773 mS/cm |
| Example 5 | Allyl | Allyl | I$^-$ | −68.1° C. | 1.32 mS/cm |
| Example 6 | Butyl | Allyl | BF$_4^-$ | −89.0° C. | 1.22 mS/cm |
| Example 7 | Butyl | Allyl | PF$_6^-$ | −85.2° C. | 1.01 mS/cm |
| Example 8 | Butyl | Allyl | [TFSI]$^{-\,(1)}$ | −90.0° C. | 1.53 mS/cm |
| Example 9 | Allyl | Allyl | BF$_4^-$ | −90.4° C. | 2.44 mS/cm |
| Example 10 | Allyl | Allyl | PF$_6^-$ | (16.7° C.)$^{(2)}$ | 1.99 mS/cm |
| Example 11 | Allyl | Allyl | [TFSI]$^{-\,(1)}$ | −91.6° C. | 2.63 mS/cm |

$^{(1)}$ (CF$_3$SO$_2$)$_2$N$^-$
$^{(2)}$ figure in parentheses is a melting point.

As is clear from Table 1, since the imidazolium compound of the present invention, which has an allyl group, has high polarity, a low glass transition temperature (Tg), and is a liquid at room temperature, it is suitable as an organic solvent. Furthermore, it can be understood that since it has high ionic conductivity, it is suitable as an electrolyte material, an organic conductive material, etc. In particular, as is clear from comparison between Examples 1, 6, 7, and 8 and comparison between Examples 4, 5, 9, 10, and 11, in the imidazolium compounds having BF$_4^-$, PF$_6^-$, or (CF$_3$SO$_2$)$_2$N$^-$ as an anion (X$^-$) the ionic conductivity improves, and they are therefore suitable as an electrolyte material, an organic conductive material, etc.

Example 12

The performance of imidazolium compounds represented by Formula (I) as a solvent was evaluated by adding 1 g of each of the 7 types of solute shown in Table 2 below to 10 mL of the imidazolium compound, and stirring at room temperature. As a control, the same evaluation was carried out using an alcoholic solvent (methanol), a halogen-containing solvent (methylene chloride), and an ether solvent (diethyl ether). Evaluation criteria were as follows. The results are given in Table 2.

Evaluation Criteria:

Poor: insoluble.

Fair: did not dissolve immediately, but dissolved in a few hours.

Good: dissolved immediately.

TABLE 2

| Solute | CH$_3$OH | CH$_2$Cl$_2$ | Et$_2$O | MeAllylImBr $^{(1)}$ | BuAllylImBr $^{(2)}$ (Example 1) | DiAllylImCl $^{(3)}$ (Example 4) |
|---|---|---|---|---|---|---|
| Glycerol | Good | Poor | Poor | Good | Good | Good |
| Urea | Fair | Poor | Poor | Good | Good | Good |
| Polyvinyl alcohol | Fair | Poor | Poor | Fair | Fair | Fair |
| Polyethylene oxide | Good | Good | Poor | Good | Good | Good |

TABLE 2-continued

| Solute | CH₃OH | CH₂Cl₂ | Et₂O | MeAllylImBr $^{(1)}$ | BuAllylImBr $^{(2)}$ (Example 1) | DiAllylImCl $^{(3)}$ (Example 4) |
| --- | --- | --- | --- | --- | --- | --- |
| Polypropylene oxide | Good | Good | Fair | Good | Good | Good |
| Carotene | Fair | Good | Fair | Good | Good | Good |
| Stearic acid | Fair | Good | Good | Good | Good | Good |

$^{(1)}$ MeAllylImBr denotes 1-methyl-3-allylimidazolium bromide.
$^{(2)}$ BuAllylImBr denotes 1-butyl-3-allylimidazolium bromide.
$^{(3)}$ DiAllylImCl denotes 1,3-diallylimidazolium chloride.

As shown in Table 2, the allyl group-containing imidazolium compounds represented by Formula (I) exhibited good solubility for a high polarity solute, a macromolecular solute, etc. In particular, it can be understood that they exhibited high solubility for the above solutes compared with diethyl ether or methylene chloride. Since the imidazolium compounds represented by Formula (I) have high affinity toward many materials as described above, they are excellent as organic solvents.

INDUSTRIAL APPLICABILITY

The imidazolium compound of the present invention can, as an ionic liquid, be used as a solvent such as a solvent for organic synthesis or a solvent for separation and extraction, or as an electrolyte material for various types of batteries, an organic conductive material, etc.

The invention claimed is:

1. An imidazolium compound represented by Formula (I) below:

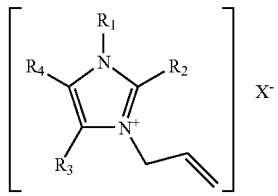

in which, $R_1$ is an alkyl group having 4 to 8 carbon atoms or an alkenyl group having 2 to 4 carbon atoms, $R_2$, $R_3$, and $R_4$ independently denote a hydrogen atom, an optionally substituted alkyl group having 1 to 10 carbon atoms, an optionally substituted cycloalkyl group having 3 to 10 carbon atoms, an optionally substituted alkenyl group having 2 to 10 carbon atoms, or an optionally substituted aryl group having 6 to 10 carbon atoms, and $X^-$ is $BF_4^-$, $PF_6^-$, $CF_3SO_3^-$, or $(CF_3SO_2)_2N^-$.

2. The imidazolium compound according to claim 1, wherein $R_1$ is an allyl group.

3. A solvent comprising an imidazolium compound represented by Formula (I) below:

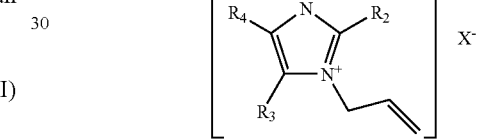

in which, $R_1$, $R_2$, $R_3$, and $R_4$ independently denote a hydrogen atom, an optionally substituted alkyl group having 1 to 10 carbon atoms, an optionally substituted cycloalkyl group having 3 to 10 carbon atoms, an optionally substituted alkenyl group having 2 to 10 carbon atoms, or an optionally substituted aryl group having 6 to 10 carbon atoms, and $X^-$ is $BF_4^-$, $PF_6^-$, $CF_3SO_3^-$, or $(CF_3SO_2)_2N^-$.

4. An electrolyte material comprising the imidazolium compound according to claim 3, wherein $X^-$ is $BF_4^-$, $PF_6^-$, $CF_3SO_3^-$, or $(CF_3SO_2)_2N^-$.

* * * * *